Figure 1:
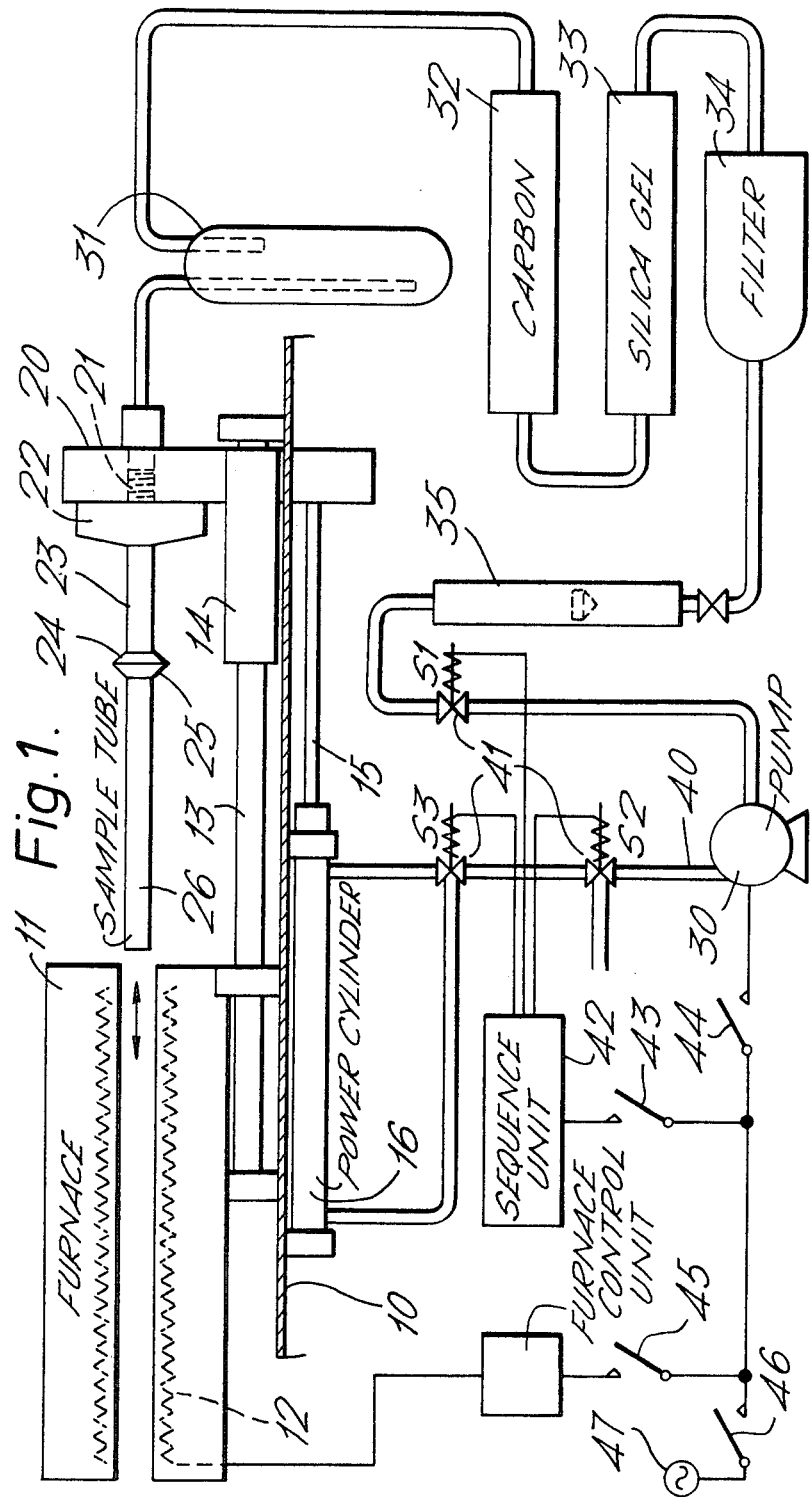

United States Patent [19]

Long et al.

[11] 4,096,867
[45] Jun. 27, 1978

[54] APPARATUS FOR PYROLYZING TOBACCO

[75] Inventors: Terence Michael Long, Yatton; Clifford Hendrik Henneveld, Oldland Common, both of England

[73] Assignee: Imperial Group Limited, London, England

[21] Appl. No.: 731,223

[22] Filed: Oct. 12, 1976

[30] Foreign Application Priority Data

Oct. 10, 1975 United Kingdom ............... 41648/75

[51] Int. Cl.² ......................... A24F 1/10; A24F 47/00
[52] U.S. Cl. ............................. 131/171 R; 73/28
[58] Field of Search ................ 131/171, 172; 73/23, 73/28

[56] References Cited

U.S. PATENT DOCUMENTS

| | | | |
|---|---|---|---|
| 3,433,054 | 3/1969 | Mutter | 131/171 R |
| 3,460,374 | 8/1969 | Parks | 73/28 |
| 3,548,841 | 12/1970 | Caugley | 73/28 X |
| 3,994,307 | 11/1976 | Loeffler | 131/171 R |

Primary Examiner—Stephen C. Pellegrino
Attorney, Agent, or Firm—Larson, Taylor and Hinds

[57] ABSTRACT

Apparatus for determining the total particulate matter in tobacco smoke comprises a reusable cartridge for holding a charge of tobacco, a pump for drawing air through the tobacco charge and through a filter, a heater to ignite the tobacco charge, and control means operable to control the heater and pump to ignite the tobacco charge, draw air continuously through the charge until it has been consumed, and thereafter reset the apparatus for consumption of a further charge of tobacco.

9 Claims, 2 Drawing Figures

APPARATUS FOR PYROLYZING TOBACCO

This invention concerns apparatus for pyrolysing tobacco.

Conventional cigarette smoking machines are useful for determining the particulate matter in tobacco smoke and for subsequent tar determination of the smoke but these machines suffer from the need to produce cigarettes before the tobacco can be smoked. Furthermore the machines suffer from the disadvantage that total time for consuming any given charge of tobacco can be considered as excessive since these machines seek to reproduce the smoker in that puffs are taken on the cigarette to consume the cigarette with a dwell time between each puff.

According to the present invention there is provided apparatus for use in determining the total particulate matter in tobacco smoke comprising a reusable cartridge adapted to hold a charge of tobacco, means for mounting the charged cartridge on a filter device whereby air drawn through the tobacco charge will pass through a filter, ignition means for igniting the tobacco charge, pump means for drawing air continuously through the charge and filter and control means operable to control the ignition means and pump means to ignite the tobacco charge, draw air continuously through the charge until it has been consumed, and thereafter reset the apparatus for consumption of a further charge of tobacco.

With apparatus as set forth above tobacco can be pyrolysed without the need first to make them into cigarettes and furthermore the total time to pyrolyse the full tobacco charge which can be the same as a standard cigarette e.g. 1 gram of tobacco is substantially reduced compared with the time to consume the same charge of tobacco on a conventional cigarette smoking machine since no dwell time is required.

Preferably the cartridge and ignition means are mounted for movement relative to one another, said control means being operable to cause relative movement between the cartridge and ignition means to effect ignition of the tobacco charge.

The ignition means may comprise a heater adapted to enclose at least a portion of the reusable tobacco cartridge including the inlet thereto, the control means maintaining the cartridge within the heater throughout the consumption of the tobacco charge. Thus the heater may be provided by an electrical element adapted to surround the cartridge which may for example be of cylindrical form.

The cartridge is preferably a glass or ceramic tube.

In a preferred form of the apparatus a filter holder is mounted on a carriage and is provided with a connection adapted to receive the cartridge, the control means being operable to move the carriage, including the filter holder and cartridge, towards the heater to dispose the cartridge within the heater and withdraw the cartridge when the charge of tobacco has been consumed.

Preferably the carriage is moved by a power cylinder operated by a pneumatic power line connected to the pump.

Figure 2:
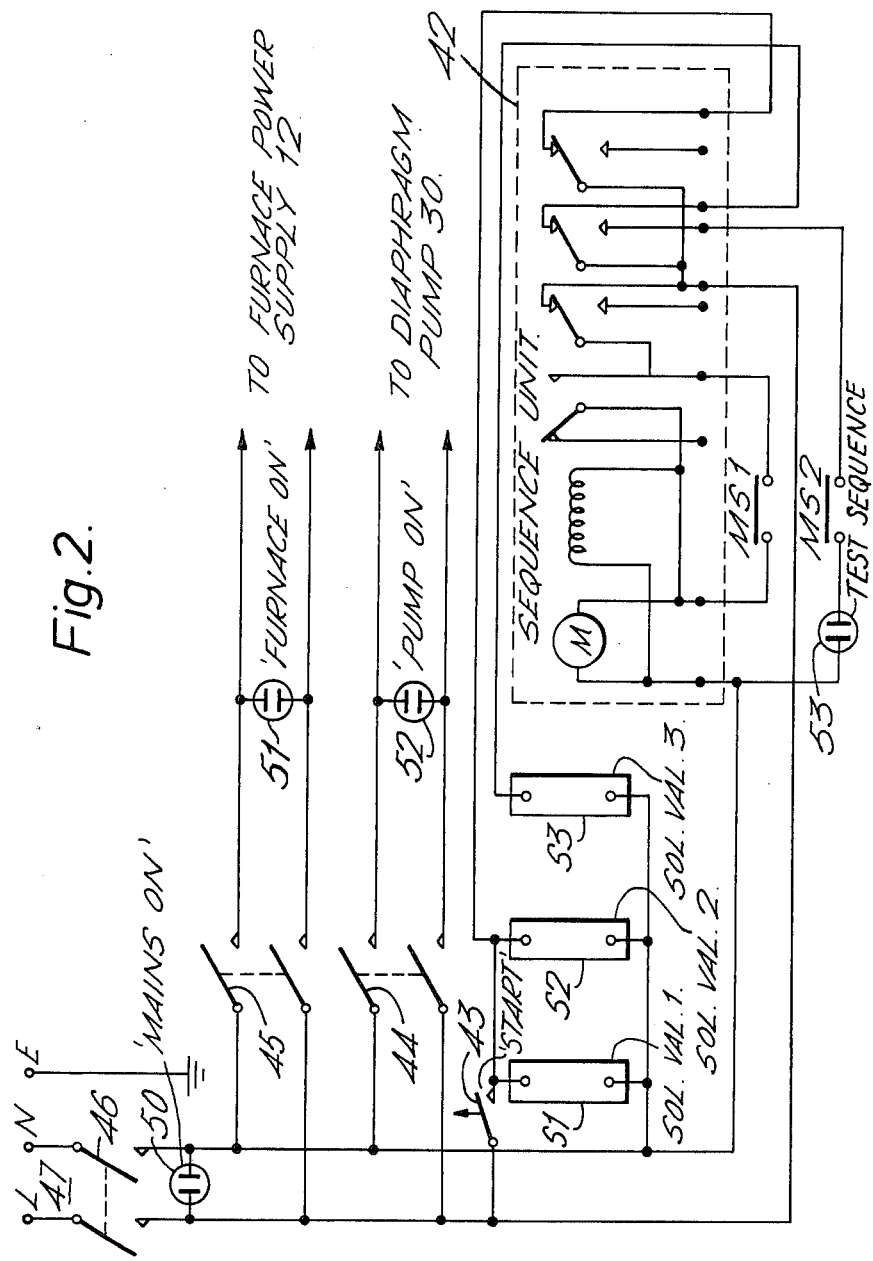

The invention is described merely by way of example with reference to the accompanying drawings in which, FIG. 1 is a block diagram representation of apparatus for pyrolysing tobacco, and FIG. 2 is a circuit diagram of electrical circuitry associated with the apparatus of FIG. 1.

In FIG. 1 the apparatus has a housing the top of which is indicated at 10. Mounted upon the housing 10 is a furnace 11 comprising a cylindrical electrical element 12 enclosed within an insulating cylinder.

Also mounted on the housing 10 are a pair of guide rods 13 on which is slidably mounted a carriage 14 adapted to be slid along the guide rods 13 by an actuating rod 15 operated in turn by a power cylinder 16.

Mounted on the carriage 14 is a mounting block 20 having a screw threaded aperture 21 adapted to receive the screw threaded boss on a Cambridge filter holder 22.

The Cambridge filter holder 22 is provided with a mounting tube 23 having at its end a ball joint 24 adapted to receive the socket end 25 of a glass tube 26.

The glass tube 26 is preselected in length and internal and external diameters and is adapted to receive a charge e.g. 1 gram of tobacco packed within the tube to represent a charge similar but not identical to that normally found in conventional cigarettes. The cartridge 26 can be snapped into the mounting tube 23 by the ball and socket joint 24/25 and the combined Cambridge filter holder 22 with the cartridge tube 26 attached thereto can be screw fitted into the mounting block 20 by the threaded aperture 21. By operating the power cylinder 16 the carriage 14 is adapted to move from the position shown in full lines in the drawing to the position shown in broken lines whereby the tube cartridge 26 is disposed within the furnace 11 to substantially its full length whereby substantially all the tube cartridge 26 is surrounded by the heating element 12.

Air is drawn through the tube cartridge 26 and the filter disposed within the Cambridge filter holder 22 to pass through the screw boss within mounting block 20 by a pump 30 which draws the air from the filter within filter holder 22 through a liquid trap 31 which condenses any large liquid particles which pass through the filter, a carbon trap 32 which removes any vapour and a silicagel trap 33 which dries the air before it reaches the pump 30. The membrane filter 34 removes any residual particulate matter and the filtered air passes through a flow meter 35 before reaching the suction pump 30. The traps 31 to 34 are adapted to protect the pump 30 since it has been found that water and particulate material passing into the pumping system affects the precision of the method by altering the pumps performance. These traps remove this deficiency.

The power for operating the power cylinder 16 is taken from the exhaust of pump 30 via line 40. A valve 41 is used to control operation of the power cylinder 16 on its forward and return strokes and this in turn is controlled by a timing device 42 via a control switch 33. Switches 44 and 45 are provided in the power lines to the pump 30 and electrical heating element 12 respectively and a mains switch 46 is provided to isolate the equipment from the mains 47.

In use the apparatus is switched on by making the switch 46 and the heater 12 and pump 30 are switched on by making the switches 45 and 44 respectively. When these components have reached steady running conditions the cartridge 26 is filled with a pre-determined weight e.g. 1 gram of tobacco which is then mounted by the ball and socket joint 24/25 in the Cambridge filter holder 22 which is mounted on the carriage 14. Upon making the switch 43 the power cylinder 16 will be actuated to move the carriage 14 whereby cartridge 26 would be moved into the furnace 11 thereby immediately igniting the tobacco charge and starting pyrolysis of the tobacco. The pump 30 will have been operating before the carriage moves thereby drawing air through the column of tobacco within the cartridge 26 and causing combustion of the tobacco as soon as it become sufficiently warm within the furnace 11. At the same time, making of the switch 43 starts the timing device 42 which is set whereby at a pre-selected time from the commencement of the operation the power cylinder 16 will be actuated to effect withdrawal of the cartridge 26 from the furnace 11 the time being set such that this motion will not be effected until all the tobacco within cartridge 26 has been pyrolysed. The time can be determined by experiment for any given charge of tobacco. Upon the completion of the cycle with the carriage 14 at the full line position shown in the drawing the filter holder 22 can be unscrewed from the mounting 20 together with the tobacco cartridge 26 and the filter paper within the holder 22 can be removed for analysis to determine the particulate matter deposited from the tobacco smoke. The tube 26 can be recharged with tobacco in a relatively short space of time for use in a further cycle.

One form of circuit diagram for use in apparatus according to the present invention is shown in FIG. 2. Referring to FIG. 2 pilot lights 50, 51, 52, 53, are provided for indicating mains, furnace, pump and test sequence respectively.

In use, with mains switch 46 made and furnace and pump both on and in steady running conditions, an automatic cycle is initiated by depressing switch 43 and holding it on. Solenoid valves S.1 and S.2 are energised to cut off air flow through the sample tube 26 and cause power cylinder 16 to move the sample tube 26 into the furnace. As the power cylinder moves rods 15, the movement makes microswitches MS1 and MS2 the first of which starts the timing sequence for sequence unit 42 and the second of which energises light 53. The switch 43 is released, which de-energises solenoid valves S.1 and S.2 maintaining sample tube 26 in the furnace and re-opening the air flow through the sample tube 26. The test is now running and the tobacco sample is pyrolysed.

At the end of the preset period, the unit 42 energises solenoid valves S.1, S.2 and S.3 whereby air passes to power cylinder 16 to retract the sample tube 26 and cut off air flow through the sample tube. The light 53 is extinguished on the return stroke of rods 15 and carriage 20.

The sequence unit resets the apparatus for the next test by de-energising solenoid valves S.1, S.2, S.3 whereby the sample tube is maintained at its withdrawn position and air flow through the sample tube is re-established. The apparatus is ready for another cycle.

By the use of the reusable glass tube 26 as a tobacco cartridge holder the need to manufacture cigarettes with the tobacco to be processed is avoided thereby reducing the time considerably for the preparation of the experiments. The particulate matter of any given tobacco blend can be determined relatively quickly by packing the tobacco within the tube and operating the apparatus whereby results will be achieved within a matter of hours compared with the many days normally taken, most of the time being occupied with the preparation of the initial cigarette product.

By drawing air through the tobacco sample on a continuous basis the time taken to pyrolyse the tobacco charge is considerably reduced compared with a conventional cigarette smoking machine since no dwell time is required between puffs.

It has been found that the air flow and furnace heat within the tube 26 are sufficient to prevent any material recondensing on the walls of the tube 26.

The cycle time of the apparatus once a steady state has been reached will vary with the size of tobacco charge used and the steady state conditions of the apparatus but in a typical example the cycle time of 6 minutes has been found adequate to pyrolyse 1 gram of tobacco where the furnace temperature is 750° C and the pump flow rate is 1 liter per minute. By this technique 9 samples an hour can be analysed.

In a comparison of the accuracy of this method as a predictor of particulate matter in tobacco smoke the experimental results were compared with those contained from cigarettes made up from the same blend of tobacco and smoked on a cigarette smoking machine. Statistical analysis of the results has indicated that the pyrolysis method described above predicted the particulate matter per gram yields to an accuracy of plus or minus 4 milligrams. This corresponded to an accuracy of plus or minus 2 milligrams per cigarette which is an acceptable experimental limit for blending work for which the above apparatus is primarily intended.

It will be appreciated that many variations on the basic form of the apparatus can be effected without departing from the invention. Thus the tobacco cartridge 26 attached to the filter holder 22 could be static and the furnace 11 could be mounted on a guide for movement relative to the tobacco cartridge. Again a different form of ignition system could be employed merely to ignite the tobacco and then allow it to burn by merely pulling air through the tobacco cartridge with no surrounding heat. With this arrangement difficulties could be encountered with the absence of a steady state condition and the maintenance of adequate heat to support combustion around the tobacco charge and condensation may be experienced on the inner surface of the cartridge tube 26.

With the present apparatus a useful and rapid assessment of particulate matter in tobacco blends is achieved with a substantial saving in time and with no significant loss of accuracy.

What we claim is:

1. Apparatus for use in determining the total particulate matter in tobacco smoke comprising, (a) a filter device, (b) within the filter device a filter for extracting particulate matter from tobacco smoke passing through the filter, (c) a reusable non-combustible cartridge for holding a charge of tobacco and having an inlet and an outlet, (d) means for mounting the cartridge when charged with tobacco on the filter device such that air passing through the tobacco charge will pass from the cartridge outlet through the filter, (e) heater means for pyrolysing the tobacco charge within the cartridge, and for enclosing at least a portion of the cartridge including the inlet tobacco, (f) pump means to draw air continuously through the tobacco charge and filter, and, (g) control means (i) for controlling the heater means to pyrolyse the tobacco charge, (ii) for controlling the pump means to draw air continuously through the charge and thence through the filter until the charge has been completely pyrolysed, and, (iii) for thereafter resetting the apparatus for pyrolysis of a further charge of tobacco within the cartridge.

2. Apparatus as claimed in claim 1 wherein the cartridge and heater means are mounted for movement relative to one another, and the control means includes means for causing relative movement between the cartridge and the heater means so that the heater means encloses said at least a portion of the cartridge.

3. Apparatus as claimed in claim 2 wherein the control means maintains the cartridge within the heater means throughout the pyrolysis of the tobacco charge.

4. Apparatus as claimed in claim 1 wherein the heater means heats the tobacco charge continuously throughout the pyrolysis.

5. Apparatus as claimed in claim 1 wherein the heater means is an electrical element adapted to surround the cartridge.

6. Apparatus as claimed in claim 1 wherein the cartridge is of cylindrical form.

7. Apparatus as claimed in claim 1 wherein the cartridge comprises a glass or ceramic tube.

8. Apparatus for use in determining the total particulate matter in tobacco smoke comprising: (a) a filter device, (b) within the filter device a filter for extracting particulate matter from tobacco smoke passing through the filter, (c) a reusable non-combustible cartridge for holding a charge of tobacco and having an inlet and an outlet, (d) connection means mounted on the filter holder for receiving the cartridge, (e) heater means for pyrolysing the tobacco charge within the cartridge, and for enclosing at least a portion of the cartridge including the inlet thereto, (f) a carriage for carrying the filter device together with the cartridge, (g) pump means to draw air continuously through the tobacco charge and filter, and (h) control means for moving the carriage including the filter device and cartridge towards the heater means to dispose the cartridge within the heater means and to withdraw the cartridge when the charge of tobacco therein has been pyrolysed.

9. Apparatus as claimed in claim 8 including: (a) a power cylinder for moving the carriage, and (b) a pneumatic power line connecting the power cylinder to the pump means, whereby the pump means provide the power to move the carriage.

* * * * *